United States Patent [19]

Bar-Shalom et al.

[11] Patent Number: 5,916,880

[45] Date of Patent: Jun. 29, 1999

[54] REDUCTION OF SKIN WRINKLING USING SULPHATED SUGARS

[75] Inventors: Daniel Bar-Shalom, Kokkedal; Niels Bukh, Hellerup, both of Denmark

[73] Assignee: Bukh Meditec A/S, Vaerlose, Denmark

[21] Appl. No.: 08/462,277

[22] Filed: Jun. 5, 1995

Related U.S. Application Data

[62] Continuation of application No. 08/293,933, Aug. 22, 1994, abandoned, which is a continuation of application No. 07/948,075, Sep. 21, 1992, abandoned, which is a continuation of application No. 07/401,459, filed as application No. PCT/DK88/00217, Dec. 21, 1988, abandoned.

[30] Foreign Application Priority Data

Dec. 21, 1987 [DK] Denmark ................. 6740/87
Sep. 9, 1988 [DK] Denmark ................. 5054/88

[51] Int. Cl.⁶ .................................................. A61K 31/70
[52] U.S. Cl. .............................. 514/53; 514/23; 514/25; 514/54
[58] Field of Search .................. 514/23, 25, 53, 514/54

[56] References Cited

U.S. PATENT DOCUMENTS

| | | | |
|---|---|---|---|
| 3,432,489 | 3/1969 | Nitta et al. | 514/53 |
| 3,577,534 | 5/1971 | Koh et al. | 514/56 |
| 4,021,544 | 5/1977 | Nair et al. | 514/54 |
| 4,486,416 | 12/1984 | Soll et al. | 514/54 |
| 4,640,912 | 2/1987 | Hausman | 514/54 |
| 4,668,665 | 5/1987 | Ishihara et al. | 514/53 |
| 4,885,281 | 12/1989 | Hanstein et al. | 514/53 |
| 4,912,093 | 3/1990 | Michaeli | 514/53 |
| 4,945,084 | 7/1990 | Packman | 514/53 |
| 4,945,085 | 7/1990 | Steiner | 514/53 |

FOREIGN PATENT DOCUMENTS

| | | | |
|---|---|---|---|
| 72795/87 | 11/1987 | Australia . | |
| 0063973 | 3/1982 | European Pat. Off. | A61K 31/725 |
| 0097625 | 6/1983 | European Pat. Off. | A61K 31/725 |
| 0097625 | 1/1984 | European Pat. Off. . | |
| 0107209 | 5/1984 | European Pat. Off. . | |
| 0130550 | 6/1984 | European Pat. Off. | A61K 31/725 |
| 0136100 | 8/1984 | European Pat. Off. | A61K 31/70 |
| 0136782 | 8/1984 | European Pat. Off. | A61K 31/725 |
| 0136100 | 4/1985 | European Pat. Off. . | |
| 0136782 | 4/1985 | European Pat. Off. . | |
| 0138572 | 4/1985 | European Pat. Off. . | |
| 0161816 | 11/1985 | European Pat. Off. . | |
| 161816 | 11/1985 | European Pat. Off. | A61K 37/24 |
| 0209142 | 7/1986 | European Pat. Off. | A61K 31/70 |
| 0107209 | 9/1986 | European Pat. Off. | A61K 31/70 |
| 0245855 | 5/1987 | European Pat. Off. | A61K 31/70 |
| 0230023 | 7/1987 | European Pat. Off. . | |
| 0245855 | 11/1987 | European Pat. Off. . | |
| 0254845 | 2/1988 | European Pat. Off. | A61K 31/715 |
| 133880 | 12/1988 | European Pat. Off. | A61K 31/70 |
| 192640 | 3/1989 | European Pat. Off. | A61K 31/70 |
| 3131811 | 4/1983 | Germany | A61K 31/725 |
| 3441835 | 10/1987 | Germany | A61K 31/725 |
| 53-009325 | 1/1978 | Japan . | |
| 54-163526 | 12/1979 | Japan . | |
| 61-028503 | 2/1986 | Japan . | |
| 62-190127 | 8/1987 | Japan . | |
| WO89/00047 | 1/1989 | WIPO | A61K 31/715 |

OTHER PUBLICATIONS

Ikre et al, Chemical Abstracts 105: 72302; (1986).
Brooks, W. Scott Jr., "Sucralfate: Nonulcer Uses", The Amer. Jo. of Gastroenterology, 80(3): 206–209, 1985.
"Rote Liste, 1986," Verzeichnis von Fertigarzneimitteln der Mitglieder des Bundesvergandes der Pharmazeutischen Industrie e.V.
PCT International–Type Search Report re Danish Application No. 6740/87, Jul. 17, 1988.
PCT International–Type Search Report re PCT/DK88/00217, dated Mar. 31, 1988.
Brooks, Jr.; Amer. J. Gastroent. 80(3):206–209 (1985).

*Primary Examiner*—Elli Peselev
*Attorney, Agent, or Firm*—Iver P. Cooper

[57] ABSTRACT

Use of a sulphated saccharide or a salt or complex thereof for the preparation of a medicament for topical application to the skin or to any non-gastrointestinal, non-oral mucosal surface of an animal or a human, including the lining of body cavities, or for injection into tissue, including joints, or implantation into surgical wounds or a body cavity of an animal or a human, for the prophylaxis or treatment of any manifestation of inflammation or infection, for the prophylaxis or treatment of non-bladder premalignant or malignant disorders, for the prophylaxis or treatment of irritation or burns of the skin, connective tissue, or non-oral mucosa, or for the prophylaxis or treatment of skin, connective tissue, or mucosal aging, or for the preparation of a medicament for systemic injection for the treatment or prophylaxis of infectious, malignant or allergic/immune disorders. The sulphated saccharide, e.g. sucrose octasulphate, may be in the form of a complex or a salt with an alkali or alkaline earth metal (e.g. Na, K, Ca, Mg or Ba) or Al, Zn, Cu, Zr, Ti, Bi, Mn or Os, or an organic base (e.g. an amino acid). The medicament may be a powder, paste, ointment, lotion, gel, cream, salve, emulsion, solution, suspension, spray, sponge, strip, plaster, pad, dressing or ostomy plate.

13 Claims, No Drawings

REDUCTION OF SKIN WRINKLING USING SULPHATED SUGARS

This is a continuation of application Ser. No. 08/293,933, filed Aug. 22, 1994, now abandoned, which is a continuation of application Ser. No. 07/948,075, filed Sep. 21, 1992, now abandoned, which is a continuation of application Ser. No. 07/401,459, filed Sep. 15, 1989, now abandoned, which is the national stage of PCT/DK88/00217, filed Dec. 21, 1988.

FIELD OF INVENTION

The present invention relates to the use of sulphated saccharides as anti-allergic, anti-infective, antiviral, immunomodulating, anti-neoplastic and anti-inflammatory agents.

TECHNICAL BACKGROUND

While it is difficult to give an adequate description of inflammatory phenomena in terms of underlying cellular events in the injured tissue, there are certain features of the process that are generally agreed to be characteristic. These include fenestration of the micro-vasculature, leakage of the elements of blood into the interstitial spaces and migration of leukocytes into the inflamed tissue. On a macroscopic level, this is usually accompanied by the familiar clinical signs of erythema, oedema, tenderness and pain. During this complex response, chemical mediators such as histamine, serotonine, leukotrienes, prostaglandines, various chemotactic factors, bradykinin, lymphokines, kinin and complement system, lysosomal enzymes and cyclic nucleotides are liberated locally. Phagocytic cells migrate into the area, and cellular lysosomal membranes may be ruptured, releasing lytic enzymes. All these events contribute to the inflammatory response.

Several drugs are employed to suppress the manifestations of inflammation, including the adrenocorticosteroids, the large group comprising the so called non-steroid anti-inflammatory drugs or NSAIDs, and drugs such as immunosuppressive agents, chloroquine, penicillamine and gold salts.

NSAIDs are chemically a heterogeneous group of drugs, mainly constituting aromatic substituted carboxylic acids. Pharmacologically, they have anti-inflammatory, antipyretic and analgetic effects, and they inhibit prostaglandin synthesis and decrease thrombocyte aggregation. The mode of action of NSAIDs is not yet fully understood, although it is known that they inhibit one or more of the mediator substances of inflammation. However, there is no good correlation between inhibition of prostaglandin synthesis and anti-inflammatory effect. The main indication for NSAIDs is rheumatic diseases, particularly where inflammatory processes in supporting tissues give rise to pain and joint-stiffness. Furthermore, the analgetic effects can be used as symptomatic pain relief in cases where the prostaglandin inhibitory effect can be utilized, such as dysmennorrhoea, urolithiasis, etc. Some of the drugs, including indomethacin, have also been used topically on the skin in the treatment of various dermatoses and as a topical anti-inflammatory agent in the eye.

The use of NSAIDs gives rise to a broad spectrum of side effects. Severe and often fatal blood dyscrasias are often seen, notably following the use of phenylbutazone, and gastrointestinal side effects are common with phenylbutazone, salicylates and indomethacin. Allergic reactions are common and may in some cases be due to prostaglandin inhibition with a resulting secondary increase in leukotriene levels. Hepatotoxicity and nephrotoxicity as well as side effects of the central nervous system are also common with these drugs.

Adrenocorticosteroids, and especially glucocorticoids, have potent anti-inflammatory effects when used in pharmacological doses. They specifically inhibit the early vascular phase of the inflammatory process by decreasing the vascular permeability and thereby granulocyte migration. Glucocorticoids also interfere with late inflammatory and reparative processes, in that they inhibit the proliferation of mesenchymal cells and the production of intercellular macromolecules, including proteoglycanes and collagen. It has been shown experimentally that glucocorticoids inhibit, far example, macrophage function, production of humoral antibodies, cellular immunity, and possibly the release of lysosomal enzymes. The indications for systemic use of glucocorticoids are apart from substitution therapy very limited, because of side effects, and should be restricted to severe inflammatory rheumatic diseases, severe cases of allergic diseases such as asthma bronchiale and status asthmaticus and cases of haematological, renal, and gastrointestinal immunological diseases. Topical use involves a much lower risk of side effects, and glucocorticoids are widely used for inhalation therapy in asthma, for topical application to the skin in nearly all cases of dermatosis and for injection in joints, bursae, tendons, etc., as well as for topical anti-inflammatory treatment of the eye, ear and nose. The most important side effects following topical use are skin and mucosal atrophy and acne, as well as microbial superinfections. In the eye, corneal ulceration, glaucoma and viral superinfections are feared and serious side effects, and steroids are in fact contraindicated in many cases.

Other anti-inflammatory drugs include penicillamine, chloroquine, gold salts and cytostatics. The main indication for these drugs is severe rheumatoid arthritis. The drugs are all given systemically, and they all exert a number of severe side effects, Thus there would seem to be a need for alternative drugs to be used both topically and systemically to suppress or modify inflammatory reactions.

Sulphated saccharides, primarily sucralfate, have previously been indicated for the treatment of gastric and duodenal ulcers (cf. U.S. Pat. No. 3,432,489; EP 161816; EP 192640) and for the treatment of emesis and diarrhoea in dogs and cats (cf. EP 133880). In radio-labelled form, sucralfate has also been used as a diagnostic agent for the imaging of gastrointestinal mucosa, since the substance binds selectively to ulcerated areas in the stomach and upper small intestine (cf. EP 107209).

The American Journal of Gastroenterology, 80(3), 1985, pp. 206–209; "Sucralfate: New Aspects in Therapy of Ulcers and Lesions" and the Second International Sucralfate Symposium Together With the World Congress of Gastroenterology in Stockholm, suggest the use of sucralfate for a variety of non-ulcer applications, including the treatment of stomatitis, post-sclerotic ulcer, reflux oesophagitis and bile reflux oesophagitis as well as for counteracting the ulcerogenic effects of aspirin.

SUMMARY OF THE INVENTION

It has surprisingly been found that polysulphated saccharides exert an anti-inflammatory effect and other very interesting effects when applied topically to the skin and to mucosal surfaces, as well as when injected systemically.

Accordingly, in one aspect, the present invention relates to the use of a sulphated saccharide or a salt or complex thereof for the preparation of a medicament for topical application to the skin or to any non-gastrointestinal, non-oral mucosal surface of an animal or a human, including the lining of body cavities, or for injection into tissue, including joints, or implantation into surgical wounds or a body cavity of an animal or a human, for the prophylaxis or treatment of any manifestation of inflammation or infection, for the prophylaxis or treatment of non-bladder premalignant or malignant disorders, for the prophylaxis or treatment of irritation or burns of the skin, connective tissue, or non-oral mucosa, or for the prophylaxis or treatment of skin, connective tissue, or mucosal aging, or for the preparation of a medicament for systemic injection for the treatment or prophylaxis of infectious, malignant or allergic/immune disorders.

The measures generally taken in conventional skin care often do not suffice for the treatment of irritations and inflammations such as eczemas, rashes and burns caused by frequent contact of the skin with an irritant. In the case of burns, fast healing of the skin is desirable as the burn is otherwise liable to become infected. This may also be the case with ostomies, which often become inflamed and occasionally ulcerated due to, presumably, extensive contact with bodily secretions, since the ostomy appliances currently used are not completely liquid-tight and since moisture is often formed where they are sealed to the skin. Persistent ulcerations or inflammations may also cause moderate to severe pain, itching, soreness and other discomfort. In spite of intensive research conducted to solve the problems connected with the treatment of diseases of the skin and mucosa and similar conditions as indicated above, no fully successful general therapy or prophylaxis has yet been devised.

The efficacy of polysulphated saccharides such as sucralfate in effecting anti-inflammatory properties is surprising in view of the fact that the published literature only discloses sucralfate for use in the gastrointestinal tract, primarily for the treatment of peptic ulcers.

Furthermore, in European Patent Application 230023, concerning the use of sulphated saccharides for the enhancement of wound healing, it is stated that sucralfate gives rise to inflammatory reactions when applied to a wound. It is also stated that low levels of 0.1–1.0 mg/ml of the polysulphated saccharide sucrose octasulphate in the form of its potassium salt, are preferred in order to avoid otherwise local haemorrhage or inflammation at the wound site. In contradiction to this, excellent anti-inflammatory effects have been obtained according to the present invention, by using sucralfate topically on skin and mucosas. According to the present invention, it has also been demonstrated that the potassium salt of sucrose octasulphate has a potent anti-inflammatory effect when applied both topically and systemically.

In an in vitro model it has been demonstrated that sucralfate in an aqueous suspension exerted a dose-related inhibition of the PHA-activated production of the cytokines interferon-gamma and interleukin-2 from human normal mononuclear cells. This suggests that sucralfate and most likely the dissolved ionized sulphated saccharide sucrose octasulphate exerts a potent anti-inflammatory effect (Example 14).

Clinical animal studies have shown that the potassium salt of sucrose octasulphate is well tolerated when applied topically into surgical wounds and when injected intravenously. In connection with surgery, a solution of 20 mg/ml of the potassium salt of sucrose octasulphate was given in a dose of 5 mg/kg body weight postoperatively to cats and dogs. There was a quick normalization of temperature and wound healing was without suppuration or inflammation. The same treatment was also effective in the management of chronic rhinitis in connection with cat's influenza, and in the treatment of a dog with aspiration pneumonia. These results suggest that the polysulphated saccharide sucrose octasulphate exerts what would seem to be potent anti-inflammatory and anti-infective effects (Example 13).

It has been possible to demonstrate experimentally in animals that the potassium salt of sucrose octasulphate exerts an anti-inflammatory effect which is comparable to that of indomethacin, when the drug is administered topically to the skin in order to protect against light-induced erythema (Example 9).

The tolerance of an aqueous suspension of micronized sucralfate 2% has been tested in a rabbit eye study. There were no signs of any irritation or any kind of inflammatory reactions in conjunctiva, cornea or eye surroundings, and it was concluded that the test article was not an eye irritant (Example 11). Clinically, this suspension has shown pronounced anti-inflammatory and anti-infective effects in the treatment of eye diseases in dogs and cats (Example 10)

In human clinical studies (Example 8) a powder containing 50% sucralfate was used in the treatment of severe diaper rash in children with a short bowel following colectomy, and later the powder was used in the treatment of ulcerative skin inflammations around ileostomies. In all cases, the effect was dramatic and suggested a strong anti-inflammatory action of sucralfate. As the next step, a wound paste containing sucralfate was tested in the management of leg ulcers. Chronic ulcers of both arteriosclerotic and venous stasis etiology were selected for the study. Approximately half of the patients showed marked wound-healing. However, the most glaring effect was the pain relief spontaneously reported by all the patients, and the decrease in tissue oedema and in skin inflammatory reactions seen in the wound surroundings.

This observation of a conceivable anti-inflammatory effect of sucralfate led to the testing of the drug administered topically as a cream or an ointment to various types of dermatoses. A marked clinical effect was seen in the management of atopic dermatitis, psoriasis and toxic hand eczema. The results suggest that sucralfate exerts an anti-inflammatory effect which is at least comparable to that of corticosteroids, in the management of steroid responding skin diseases (Example 8).

The unique combination of anti-inflammatory activity with that of a wound-healing or tissue stimulating effect, (as opposed to hitherto known anti-inflammatory drugs, such as the steroids and NSAIDs) makes sucrose octasulphate and probably the entire group of polysulphated saccharides an interesting new group of compounds to be used as an alternative to conventional anti-inflammatory drugs. Furthermore, the extremely high tolerability of sucralfate, which is the aluminium complex of sucrose octasulphate, as documented by the total absence of side-effects following its use in the treatment of peptic ulcer, and the very high tolerability of both sucralfate and sucrose octasulphate when used topically on the skin and mucosa makes sucrose octasulphate, and probably other polysulphated saccharides, very attractive as alternatives to conventional anti-inflammatory drugs.

It is furthermore contemplated that sulphated saccharides such as sucrose octasulphate modify or inhibit inflammatory reactions and/or stimulate tissue regenerative processes via other, not yet fully understood mechanisms.

It has been observed that one sulphated saccharide, sucralfate, when used internally in the treatment of peptic ulcers, binds preferentially to the surface of the ulcer. It is currently believed that this is a property common to sulphated saccharides, and that this binding is the result of an ability of sulphated saccharides to bind to proteoglycanes and hyaluronic acid. These structures are components of the surface of many cells, and they protect and stabilize the cell so the exterior cell surface remains intact. In other cases, e.g. in dermis and supportive tissue, proteoglycanes and hyaluronic acid form a protective matrix in which cells are embedded. Furthermore, it is known that certain sulphated saccharides, e.g. heparan sulphate, dextran sulphate and xylose sulphate, are hyaluronidase inhibitors.

Hyaluronidases are enzymes which catalytically cleave the glycosidic bonds of hyaluronic acid and glycosaminoglycanes. The decomposition of hyaluronic acid and glycosaminoglycanes by hyaluronidases therefore leads to exposure of the cells, via destruction of the cell surface or the supportive matrix substance, as well as to damage from various agents such as pathogens, inflammatory mediator substances, inflammatory agents and corrosive agents. Thus it is believed that by inhibiting hyaluronidases, sulphated saccharides promote the regeneration of the cell surface and the protective connective tissue matrix, and thereby effect an anti-inflammatory and tissue regenerative action.

Decomposition products of hyaluronic acid and glycosaminoglycanes may also act as mediator substances of inflammation themselves, and via inhibition or modification of such decomposition, sucrose octasulphate and other sulphated saccharides may inhibit or modify inflammatory reactions and facilitate and modify tissue regeneration.

Thus it is contemplated that the above-mentioned pharmacological effects of sucrose octasulphate and other sulphated saccharides result in a "strengthening" of epithelial and mucosal linings. Apart from effecting an anti-inflammatory action, this strengthening of the exterior cell surface and connective tissue cell matrix will also make it more difficult for bacteria and virus to penetrate and colonize the cells and the tissue. Instead of a direct antimicrobial effect, an indirect effect will thus be obtained by applying sucrose octasulphate or other sulphated saccharides to mucosal and epithelial surfaces. Thus the compounds may be used topically in the treatment of bacterial, viral or mycotic infections of skin and mucosa. The antimicrobial effect may possibly also be utilized by applying sucrose octasulphate or other sulphated saccharides directly to supportive tissues in connection with surgery. Many infections spread in the tissue by means of hyaluronidases produced or induced by the pathogens themselves. It is contemplated that the hyaluronidase inhibiting effect of sucrose octasulphate and other polysulphated saccharides prevents the spreading of such infections.

Such anti-inflammatory and anti-infective actions may furthermore be utilized when implanting or inserting medicotechnical devices into the body. By incorporating sucrose octasulphate or another sulphated saccharide into the surface coating of a device or into the material of the device itself, it is contemplated that infections and inflammatory tissue reactions, including thrombophlebitic reactions, around the device can be diminished (see Example 12). Examples of devices where such a technique could be used are urethral catheters, peritoneal dialysis catheters, e.g. dural and spinal catheters, venous and arterial catheters, electrodes, breast prostheses, pacemakers, middle ear tubes, eye lenses, vascular prostheses, hip prostheses, etc. Other uses may comprise coating of any material to be placed directly on the skin or mucosa for longer periods, such as ostomy plates, external prostheses, etc.

It is furthermore contemplated that the "strengthening/modifying" effect of sucrose octasulphate and other sulphated saccharides on the cell surface may be utilized in the management of malignant disorders. Examples are treatment of superficial skin and mucosal malignancies such as basal cell carcinomas, cervical dysplasia and carcinoma, etc. by topical application of sucrose octasulphate or another sulphated saccharide on the lesions, and possibly also by placing depot preparations which release sucrose octasulphate or other sulphated saccharides into the surrounding tissue in connection with surgery for malignant diseases. It is also contemplated that injection into the bloodstream of sucrose octasulphate or other suitable preparations of sulphated saccharides may be effective, via their cell surface modifying action, against diseases characterized by infection of the blood cells with virus or viroids, such as leukaemia and other types of haematological or systemic malignant diseases, against allergic blood dyscrasias, against AIDS and other types of viral infectious diseases, against bacterial septicaemia and against malaria and other types of infectious diseases affecting the blood cells. It is also contemplated that systemic administration of sucrose octasulphate or other sulphated saccharides may be used in the management of immune diseases, in order to modify systemic immunological responses. Examples of the latter type are collagen diseases such as LED (lupus erythematosus disseminatus), dermatomyositis, amyloidosis, rheumatoid arthritis, scleroderma, sarcoidosis, etc.

It is furthermore contemplated that sucrose octasulphate and other sulphated saccharides might be useful as an addition to the growth medium of a cell culture because of their cell surface modifying action.

The present invention further relates to a pharmaceutical preparation, in particular for any of the uses stated above, which comprises sucrose octasulphate or another sulphated saccharide or a salt or complex thereof alone or together with a pharmaceutically acceptable excipient.

In a still further aspect, the invention relates to a method of preventing or treating any manifestation of inflammation or infection of the skin or any non-gastrointestinal, non-oral mucosal surface of an animal or a human, including the lining of body cavities, for preventing or treating non-bladder premalignant or malignant disorders, for preventing or treating irritation or burns of the skin, connective tissue, or non-oral mucosa, or for preventing or treating skin, connective tissue, or mucosal aging, the method comprising applying to the skin, mucosa or tissue a therapeutically or prophylactically effective amount of a sulphated saccharide or a salt or a complex thereof; and a method of preventing or treating infectious, malignant, or allergic/immune disorders in an animal or a human, comprising injecting a therapeutically or prophylactically effective amount of a sulphated saccharide or a salt or complex thereof systemically into the animal or the human.

Interesting embodiments of the aspects of the invention appear from the appended claims.

DETAILED DISCLOSURE OF THE INVENTION

The sulphated saccharide used in accordance with the invention may be a monosaccharide, for instance xylose, fructose or glucose, an oligosaccharide, in particular a disaccharide such as sucrose, lactose, maltose or cellobiose, or a polysaccharide such as dextran, heparan, dermatan, proteodermatan, heparin, chondroitin, amylose, glucosamine, glucosaminoglycane and a mucopolysaccharide or a subunit thereof.

In certain cases, it may be an advantage to use the sulphated saccharide in combination with another wound-healing substance such as a non-sulphated polysaccharide, for instance hyaluronic acid, vide Example 7.

The saccharide is preferably a polysulphated or persulphated saccharide, which means that two or more, possibly all, sulphur-containing moieties are present as substituents on the carbohydrate moiety.

In some cases, the sulphated saccharide may be complexed with or form a salt with a metal, e.g. an alkali or alkaline earth metal such as Na, K, Ca, Mg or Ba, or Al, Zn, Cu, Zr, Ti, Bi, Mn or Os, or with an organic base (e.g. an amino acid). The currently preferred salts are potassium and sodium salts.

Preferred oligosaccharides are mono- and disaccharides. Most preferably, the composition of the invention contains a persulphated disaccharide, optionally sucrose octasulphate.

The substance may, for instance, be prepared as disclosed in EP 230023.

Although there may be cases where the sulphated saccharide may be administered as such, it will typically be compounded with one or more pharmaceutically acceptable carriers or excipients to present it in a form which is suitable for topical or systemic application. In other words, it will be in the form of a liquid, semi-solid or solid topical or systemic preparation such as a powder, paste, ointment, lotion, gel, cream, salve, emulsion, solution, suspension, spray, sponge, strip, plaster, pad, dressing or ostomy plate.

For topical application, the preparation may be formulated in accordance with conventional pharmaceutical practice with pharmaceutical excipients conventionally used for topical applications such as pectin, gelatin and derivatives thereof, polylactic acid or polyglycolic acid polymers or copolymers thereof, cellulose derivatives such as methyl cellulose, carboxymethyl cellulose or oxidised cellulose, guar gum, acacia gum, karaya gum, tragacanth gum, bentonite, agar, carbomer, bladderwrack, ceratonia, dextran and derivatives thereof, ghatti gum, hectorite, ispaghula husk, polyvinylpyrrolidone, silica and derivatives thereof, xanthan gum, kaolin, talc, starch and derivatives thereof, paraffin, water, vegetable and animal oils, polyethylene, polyethylene oxide, polyethylene glycol, polypropylene glycol, glycerol, ethanol, propanol, propylene glycol, (glycols, alcohols), fixed oils, sodium, potassium, aluminium, magnesium or calcium salts (such as the chloride, carbonate, bicarbonate, citrate, gluconate, lactate, acetate, gluceptate or tartrate).

The preparation of the invention may also contain other additives such as emulsifiers, stabilizing agents, preservatives, etc.

For use in the treatment of respiratory diseases, the preparation of the invention may be formulated as a powder, solution or suspension for inhalation, a spray formulation or a similar appropriate formulation.

Plasters, sponges, strips, pads or other dressings may be prepared by impregnating a dressing material such as cotton wool or gauze or a polymeric substance with a solution or suspension of the sulphated saccharide followed by drying. Alternatively, a paste, lotion, cream or gel containing the sulphated saccharide may be spread over the dressing material, conveniently immediately prior to use.

For the treatment of mucosa, e.g. the vaginal, nasal and ocular mucosa, the preparation of the invention may for instance be formulated in the form of a vaginal suppository, gel, ointment, solution or suspension or vaginal insert, a nasal solution, suspension, gel, ointment or a nasal insert or an eye solution, suspension, gel, ointment or an eye insert. Such formulations may be prepared in accordance with conventional pharmaceutical practice using conventional excipients such as some of those mentioned above.

The pharmaceutical preparation of the invention generally comprises the sulphated saccharide in an amount of 0.001–99%, typically 0.01–75%, more typically 0.1–20%, especially 1–10% by weight of the total preparation. In particular, when the sulphated saccharide is sucrose octasulphate, a preferred concentration thereof in the preparation is often 0.5–50%, especially 0.5–25%, such as 1–10%. It is suitably applied 1–10 times a day, dependent on the type and severity of the condition to be treated.

The concentration of the sulphated saccharide to be used in each particular case will of course depend upon the type of preparation and the intended use, but also on the solubility characteristics of the sulphated saccharide and, for sparingly soluble and substantially insoluble sulphated saccharides, on the particle size thereof; the smaller the particle size, the faster will be the distribution of even sparingly soluble or even substantially insoluble sulphated saccharides or complexes thereof. Insoluble or sparingly soluble salts or complexes of sulphated saccharides are preferably used in the form of a fine powder, for example having a particle size of 200 $\mu$m or less, such as 100 $\mu$m or less. Examples of very small particle sizes which may be desirable for certain purposes are e.g. 50 $\mu$m or less, such as 20 $\mu$m or less, in certain cases 10 $\mu$m or less, such as 5 $\mu$m or less.

The preparation may contain other active agents than the sulphated saccharide, such as antibacterial agents, antiviral agents, anti-parasitic agents, sun protective agents, vitamins and vitamin derivatives or analogues, antineoplastic agents, antimycotic agents, antifibrinolytic agents, blood coagulation modifying agents, antiseptic agents, analgesics, topical anesthetics or antiinflammatory agents.

As mentioned above, the sulphated saccharide is indicated for use in connection with any skin, mucosa or tissue condition involving irritation, inflammation or burns, or for the prevention of ulceration of the skin. Furthermore, it has been found particularly advantageous to treat skin conditions caused by contact with an external chemical agent (e.g. an allergen or a corrosive substance such as an acid or a base) or with body secretions such as urine, sweat or gastrointestinal secretions, or by external pressure, or by heat, or ionizing radiation, or light (which in the present specification and claims includes ultraviolet light) by means of the sulphated saccharide, or to add the sulphated saccharide as a prophylactic measure to prevent skin damage resulting from these agents or secretions.

Examples of particular conditions for which use of the sulphated saccharide is therapeutically or prophylactically indicated include:

Skin diseases, (including lips, vaginal mucosa and perianal areas), such as:

Miliaria, defined as an acute inflammatory pruritic eruption resulting from obstructed sweat glands, often precipitated by even minor skin irritation, e.g. application of adhesive plasters or excessive moist heat (sunburn, diaper, exercise).

Intertrigo, defined as acute superficial inflammation of opposing skin surfaces, characterized by erythema, abrasion, maceration, and, in some cases, superficial fissuring.

Pruritus, defined as a generalized or localized itching sensation, which the patient instinctively attempts to relieve by scratching.

Acne and rosacea, defined as inflammation of the sebaceous glands and characterized by seborrhoea comedones, pustules, papules and nodules.

Superficial bacterial skin infections such as erythrasma; superficial fungal infections such as ringworm and candida; viral infections such as herpes simplex, herpes zoster, measles, varicella, warts, condyloma acuminata, vaginosis, either non-specific or caused by mycoplasma, chlamydia, candida, Thrichomonas, etc.

Dermatitis, defined as an acute or chronic superficial inflammation of the skin, whether microbially infected or not, characterized by erythema, oozing, crusting, scaling, and sometimes by vesicles. Included are contact dermatitis, atopic dermatitis, seborrhoeic dermatitis, neurodermatitis, lichen simplex, drug eruption, erythema nodosum, erythema multiforme, pityriasis rosacea, lichen planus, psoriasis, ichthyosis, stasis dermatitis and chronic dermatitis of the hands and feet.

Acute sunburn and other superficial burns, and protective against sunburn.

Skin irritation secondary to the presence directly on the skin of a prosthetic device, diaper, ostomy pad or similar, bandage, plaster, electrode, catheter, etc.

Prophylactically against pressure sores.

Boils, furuncles, carbuncles, hidrosadenitis, and fistules.

Hemorrhoides, perianal pruritus and vulvitis.

Cosmetically against wrinkles and aging skin, both as active and prophylactic treatment, and against dandruff.

Respiratory diseases such as:

Allergic rhinitis, characterized by seasonal or perennial sneezing, rhinorrhea, nasal congestion, and often conjunctivitis and pharyngitis, Acute rhinitis, characterized by oedema of the nasal mucosa, nasal discharge and obstruction. In most cases caused by a common virus.

Pulmonary diseases, such as intrinsic or extrinsic asthma bronchiale, pulmonal inflammatory reactions secondary to chronic bronchitis, pneumoconioses, pulmonary fibrosis, Goodpasture's syndrome, etc.

Ear, nose and throat disorders such as:

Acute external otitis, furunculosis and otomycosis of the external ear.

Traumatic and infectious myringitis.

Acute eustachian salpingitis.

Acute serous otitis media.

Acute and chronic sinusitis.

Eye diseases such as:

Oedema in the eye region caused by trauma or foreign bodies, or postoperative inflammation.

Eyelid allergies and blepharitis; hordeolum and chalazion.

Acute and chronic catarrhal conjunctivitis of any microbial etiology.

Allergic (vernal) conjunctivitis.

Trachoma.

Scleritis, episcleritis.

Superficial punctate keratitis, dendritic (herpetic) keratitis, disciform keratitis, corneal wounds.

Iritis, iridocyclitis.

Systemic i.v. therapy as antiallergic/immunomodulating, anti-inflammatory therapy in:

Connective tissue disorders such as:

Systemic lupus erythematosus, polyarteritis nodosa, scleroderma, polymyositis, dermatomyositis, rheumatoid arthritis.

Allergic/immune disorders such as:

Anaphylaxis, serum sickness, hemolytic anaemia, allergic/toxic agranulocytosis.

Malignant disorders such as:

Acute leukemia, chronic myelocytic leukemia, chronic lymphocytic leukemia, Hodgkin's disease, lymphosarcoma, myeloma, metastasing carcinoma of any origin, metastasing melanoma.

Infectious disorders such as:

AIDS, bacterial septicaemia, systemic fungal infections, Richettsial diseases, toxic shock syndrome, infectious mononucleosis, cytomegalovirus infection, influenza, poliomyelitis, malaria, Leishmaniosis, Trypanosomiasis, Toxoplasmosis, Lassa Fever, Yellow Fever.

Topical injection or implantation therapy or topical application therapy in premalignant or malignant disorders such as:

Cancer in situ colli uteri, cervical carcinoma, endometrial carcinoma, at the site of surgery for cancer of any origin, basal cell carcinoma.

Injection therapy in tissue, bone, joint or musculoskeletal disorders, such as:

Tendinitis, tenosynovitis, tendofibrositis, bursitis, fibromyositis, myositis, fibrositis and epicondylitis, strains and sprains, twisting, dislocation, luxation, carpal tunnel syndrome, fascitis, synovitis in rheumatoid arthritis, infectious arthritis, monoarthritis in arthritis urica, spondylitis, chondrocalcinosis, Reiter's syndrome, osteitis, osteomyelitis.

Tissue implantation in connection with surgical procedures, in order to achieve anti-infective effects and anti-inflammatory, tissue organization/regeneration effects at the site of surgery.

As previously stated, it has been observed that sucralfate, when used internally in the treatment of gastric ulcer, binds preferentially to the surface of the wounded mucosa, and it is currently believed that this is a property common to polysulphated saccharides. If the mucosal lining is disrupted, as with an ulcer or a malignant process, polysulphated saccharides will accordingly bind specifically to that area. This property may be utilized in X-ray diagnostics, by using the barium, zirconium, titanium, osmium salt or other X-ray dense formulations of either sucrose octasulphate or other polysulphated saccharides.

The invention is further illustrated by the following non-limiting examples.

EXAMPLE 1

A topical powder preparation was prepared from the following ingredients:

| Sucralfate* | 30 g |
|---|---|
| Pectin | 10 g |
| Gelatin | 10 g |
| Carboxymethylcellulose | 10 g |

*Provided by Abic Laboratories, Israel, in finely divided form.

The finely divided sucralfate (particle size 2–100 μm) was thoroughly mixed with the other ingredients in finely divided form (particle size <250 μm) to produce a powder.

EXAMPLE 2

A topical ointment preparation was prepared from the following ingredients:

| | |
|---|---|
| Sucralfate | 30 g |
| Pectin | 10 g |
| Gelatin | 10 g |
| Carboxymethylcellulose | 10 g |
| Fractionated coconut oil | 60 g |

The finely divided sucralfate (particle size 2–100 μm) was thoroughly mixed with the other ingredients in finely divided form. The fractionated coconut oil was added to the resulting powder to a suitable consistency and a substantially homogeneous dispersion of the particulate components.

EXAMPLE 3

A topical ointment preparation was prepared from the following ingredients:

| | |
|---|---|
| Sucralfate | 30 g |
| Hyaluronic acid | 0.6 g |
| Pectin | 10 g |
| Gelatin | 10 g |
| CMC | 10 g |
| Fractionated coconut oil | 60 g |

The finely divided sucralfate (particle size 2–100 μm) was thoroughly mixed with the other ingredients in finely divided form. The fractionated coconut oil was added to the resulting powder to a suitable consistency and a substantially homogeneous dispersion of the particulate components.

EXAMPLE 4

A topical eye preparation was prepared from the following ingredients:

| | |
|---|---|
| Sucralfate* | 2% |
| Carbopol 934 | 0.5% |
| Mannitol | 5% |
| Benzalkoniumchloride | 0.01% |
| Sodium EDTA | 0.05% |
| Sodium hydroxide q.s. | ad pH 6 |
| Sterile water | ad 100% |

*Micronized sucralfate (particle size 10 μm), provided by Guilini Chemie, W. Germany.

EXAMPLE 5

Eye preparation

An eye preparation was prepared from the following ingredients:

| | |
|---|---|
| Sucralfate* | 2% |
| Propyl methyl cellulose | 0.35% |
| Benzalkonium chloride | 0.01% |
| Sodium EDTA | 0.05% |
| Sodium chloride | 0.8% |
| Sterile water q.s. | |

*Micronized (10 μm), provided by Guilini Chemie Ludwigshafen, W. Germany.

EXAMPLE 6

A topical preparation for skin and mucosa was prepared by mixing 5% by weight of a sucralfate powder (particle size 50–100 μm, provided by Guilini Chemie, W. Germany) with a mixture of cetanole, adeps lanae purificatae, isopropyl myristas, Tween 60, Span 60, dimeticone, glycerol, sorbic acid and sterile water.

EXAMPLE 7

A) A topical preparation for mucosa and skin was prepared from the following ingredients:

| | |
|---|---|
| Sucralfate powder* | 5% |
| Paraffin oils, glycerine, cetyl alcohol | 55% |
| Quarternary ammonium compounds | 0.7% |
| Stearyl alcohol | 3% |
| Eucalyptus oil q.a. | |

*Micronized sucralfate (≦10 μm), provided by Guilini Chemie, W. Germany.

EXAMPLE 8

Human Clinical Trials

A) Two babies (a boy and a girl) who had been operated on to correct congenital megacolon (Hirschsprung's disease) developed a severe rash with erythema, inflammation and pustules (presumed to be caused by contact with digestive enzymes and possibly acid due to the shortening of the intestines). The preparation of Example 1 was applied to the affected skin at each change of diapers. After one day of treatment the condition had improved dramatically, and the rash disappeared completely after two to three days of treatment. The treatment was continued for six months. For the first four months after the operation, interruptions in the daily application of the sucralfate-containing powder resulted in recurrence of the rash. After six months, however, it was possible to discontinue the treatment with occasional resumption after, for instance, diarrhea.

B) Ten oncological patients with ileostomies who had developed ulcerations around the ileostomies were treated with the preparation of Example 1. A control group of ten other patients who had similarly developed ulcerations around ileostomies were treated with a powder preparation containing equal amounts of pectin, gelatin and carboxymethylcellulose (i.e. the preparation of Example 1 without any sucralfate). In each case, the powder was applied at each change of the ostomy bag for two weeks.

After three days of treatment none of the patients in the group treated with the sucralfate-containing powder showed any ulceration around the ileostomy, whereas 7 of the patients in the control group did to greater or lesser extent. After two weeks of treatment one of the patients in the group treated with the sucralfate-containing powder had had ulcerations for two periods each lasting three days, one of the patients had died, and the others were free from ulceration for the entire period. In the control group, two patients were free from ulceration at all times, whereas all the others had ulcerations/severe irritation lasting two days or more. Two of the patients had ulcerations around the ileostomy for the entire period.

Based on these trials it was concluded that the preparation of the invention may successfully be used in the treatment of ulcerations and similar conditions of the skin caused by gastrointestinal secretions. Trial B) shows that sucralfate is responsible for the improvement rather than any other ingredient in the composition.

C) Fourteen elderly patients (aged 49–86 years, mean 70), with chronic leg ulcers of either ischaemic or venous stasis etiology, were treated with the preparation of Example 2. At the start of the therapy, surgical debridement was made. The wounds were then filled up with the paste, and according to the nature of the surrounding skin, the wound area was covered with either a plastic film or with parchment paper. At the weekly changes, surplus paste was carefully removed so as not to destroy granulation tissue, if present, and the treatment was repeated, i.e. the wound was filled with new paste and the wound area covered. In seven patients, there was a complete or nearly complete wound healing after two to three months of therapy. The wound healing effect was evaluated by measuring the size of the wound at each control. During the first month of therapy, there was a reduction in the size of the wound in nine cases, the initial wound size being reduced by an average of 76% in the nine cases. In three cases there was no effect on wound size, and in the last two cases this measurement was not made. Pain in the wound was assessed on a scale from 0=absent to 3=severe. In all cases there was a marked pain relief, typically within a few hours after application of the wound paste. It was observed that the oedema in the surrounding tissue decreased and that the macerated and inflamed skin in the wound surroundings healed. Most of the wounds had fibrin, pus, and yellow necrosis at the start. They had in all cases turned into "red wounds" after treatment, with clean red granulation tissue free of infection. The mean scores for pain and eschar at baseline and during the following four weeks of treatment are shown in Table 1:

TABLE 1

| | Mean score (0 = absent to 3 = severe) | | | | |
|---|---|---|---|---|---|
| | Baseline | Week 1 | Week 2 | Week 3 | Week 4 |
| Pain: | 2.21 | 1.50 | 1.31 | 1.18 | 1.00 |
| Eschar: | 1.92 | 1.38 | 1.19 | 0.67 | 0.60 |

It would seem that sucralfate used topically on chronic leg ulcers exerts a definite wound-healing effect. At the same time, there was a marked anti-inflammatory effect of the sucralfate wound paste, in that oedema in the tissue decreased and inflamed and macerated skin around the wound healed.

D) The anti-inflammatory effect of sucralfate on various types of dermatosis was evaluated in adult patients with atopic dermatitis, psoriasis, toxic hand eczema and folliculitis. The preparation comprised 5% by weight of sucralfate powder mixed in a fatty vehicle containing herbal extracts of chamomile (6%) and arnica (4%). The ointment was applied morning and evening. Table 2 summarizes the demographic data and diagnostics of treatment of the patients included in the study.

TABLE 2

| Diagnosis | No. of Patients | Sex | Age | Drug tested for |
|---|---|---|---|---|
| Atopic dermatitis | 8 | F | 18–44 | 1–8 months |
| Atopic dermatitis | 6 | M | 21–33 | 1–5 months |
| Psoriasis (universal) | 3 | M | 33–39 | 1–4 months |
| Psoriasis (universal) | 5 | F | 19–28 | 3–8 months |
| Psoriasis (local) | 6 | M | 19–31 | 1–6 months |
| Psoriasis (local) | 7 | F | 23–33 | 1–8 months |
| Toxic hand eczema | 5 | F | 35–48 | 5–8 months |
| Folliculitis (beard) | 7 | M | 30–60 | 2–3 months |
| Anal-vulval pruritus | 4 | F | 48–71 | 4 months |

Topical application of sucralfate ointment twice daily resulted in improvement or complete cure in all 51 cases. All of the patients except two females with local psoriasis and seven males with beard folliculitis had previously received extensive topical treatment with steroids. The patients with atopic dermatitis had disease histories of 10–20 years, and they all suffered from rebound phenomena following use of steroids. There was a marked improvement after 10 days of treatment with sucralfate ointment, and 10 out of the 14 patients with atopic dermatitis have been cured in the sense that the patients have been completely free of dermatotic symptoms during treatment periods of up to 8 months. Patients with psoriasis have shown improvement after 2 to 4 weeks of treatment, and the improvement has in all cases been maintained for the entire treatment period. Patients with toxic hand eczema have shown improvement after one week, and the patients have been completely cured in three cases. A good effect has been shown with beard folliculitis over a treatment period of 2 to 3 months, and females with vulvovaginitis symptoms were freed of their pruritus. No side effects have been seen during treatment with sucralfate ointment covering a total period of 156 patient months.

In a few clinical cases, a marked antimicrobial effect has been observed with topical application of sucralfate to skin and mucosas:

E) Two patients with a superficial fungal skin infection (ringworm) received the sucralfate preparation of Example 6. After one day there was a marked improvement, and after three days of application of the sucralfate preparation two times a day, the skin was completely free of clinical signs of any fungal infections.

F) Two females with severe and long standing non-specific colpitis of suspected infectious etiology received the sucralfate preparation of Example 7. The ointment was applied twice a day to the vaginal mucosa. In both cases there was a complete clinical cure after two weeks of therapy. Both patients had received almost every kind of topical therapy, including steroids and antimicrobials, without effect for several years.

G) The sucralfate ointment of Example 6 has been used topically on herpes labialis. The ointment was applied three to six times daily, and the treatment was started as soon as possible after the herpetic eruption. Four young females have been evaluated, and in all four cases treatment has been successful in the sense that pain was reduced and there was a reduction in eruption of blisters. The skin was completely healed within two to four days after the start of treatment.

H) The sucralfate ointment of Example 6 was tested in the treatment of acne vulgaris. Three females aged 16–20 years applied the ointment topically morning and evening. There was a marked reduction in the inflammatory reaction of the skin after one day of treatment, and after one week there was a reduction in the number of follicles. All three patients had previously tried many kinds of anti-acne therapy, including vitamin A and systemic antibiotics. Sucralfate resulted in a more lasting effect, and there have been no rebound phenomena during treatment periods of up to 3 months.

I) The sucralfate ointment described in Example 8 D) was tested on facial wrinkles around the eyes. Three females aged 38–45 have used the ointment twice daily, and a beneficial effect has been reported after 1–2 weeks of treatment.

EXAMPLE 9

Ultraviolet sunburn (erythema) study in guinea pigs:

Twelve young adult SPF albino guinea pigs (male and female, 10 weeks of age, body weight 350–400 g) of the Dunkin Hartley strain, from Moellegaard Breeding Centre Ltd., were used.

The animals were housed in opaque PPL (type IV) cages, two or three to a cage, males and females separated. They had free access to a pellet diet, "3113 Altromin", and vitamin C enriched tap water. The room temperature was set at 21° C.±2° C. and the relative humidity at 55%±15%. The air was changed 6 times an hour, and the light was on from 06 to 18 h. The acclimatization period was one week.

The control substance was Indomethacin as a 10% by weight suspension in PEG 400, and the test substance was sucrose octasulphate in the form of the potassium salt thereof as a 1, 3 and 10% by weight suspension in PEG 400. The vehicle control was PEG 400.

The day before treatment, both flanks of the animals were clipped free of hair and shaved with an electric razor. The next day, the unanaesthetized animals were restrained on the side opposite that which was to be exposed to the light. A rubber sheet with two openings with a diameter of 4 cm (each about 12.5 cm$^2$), was placed on the clipped and shaved flank of each animal and the rest of the body was covered in order to protect the animal from the UV-light, except for the two treatment sites. Two guinea pigs at a time were subsequently exposed to light from ultraviolet lamps (T1 20/12, UVB, Philips), at a distance of 6 cm for 20 minutes.

In the center of the two erythema treatment sites (each about 5 cm$^2$), 0.05 ml of the test substance, the control substance or the vehicle, respectively, was applied. After application, the substance was massaged into the skin for a period of about 30 sec. with the tip of the finger. To measure prophylactic effectiveness, the application took place 30 minutes before the UV-exposure.

Each of the 24 flanks of the 12 animals in the positive test group were treated with both the test substance and either 10% Indomethacin or vehicle. The application of the two substances per flank was performed according to a special system to eliminate variation due to anatomical or structural differences of the epidermis of the flanks and to support the quality of the blind reading.

Two, four, six and twenty-four hours after termination of the UVB-light exposure, the treatment sites were read and evaluated according to the following scale:

| Erythema (ER) reduction | Score |
| --- | --- |
| No visible sign of ER | 0 |
| Barely discernible ER | 1 |
| Faint non-confluent ER | 2 |
| Marked non-confluent ER | 3 |
| Marked non-confluent or confluent zones of ER beyond application area | 4 |
| Homogeneous ER | 5 |
| Homogeneous ER beyond application area | 6 |

The animals were read blindly, and the erythema reduction scores for each substance were averaged. The vehicle control average has been subtracted from the positive control average and test substance average, respectively, to yield the relative erythema reduction activity.

The following erythema reduction activity was found:

| | |
| --- | --- |
| Vehicle (PEG 400) | 0% |
| Positive control (Indomethacin 10%) | 100% |
| Test 1% (sucrose octasulphate) | 5% |
| Test 3% (sucrose octasulphate) | 22% |
| Test 10% (sucrose octasulphate) | 62% |

A dose-response relationship was revealed with the test substance in question, and in spite of the very small number of animals, it must be concluded that in this experiment, sucrose octasulphate reduces the erythema on sunburned (UVB-exposed) skin of guinea pigs to the same extent as indomethacin.

EXAMPLE 10

Sucralfate eye and nose drops in dogs and cats

The preparation of Example 5 was evaluated in 20 dogs with chronic red eyes presumably due to infections and allergic reactions. The eye drops were applied to fornix inferior morning and evening. Fourteen out of twenty animals responded to the treatment, 5 of which had failed to respond to previous treatment with topical eye antibiotics including chloramphenicol and fusidine. The effect was seen after 1–5 days and the treatment period was in most cases 2–3 weeks. The same preparation was used in the treatment of chronic congestion of the tear canals of purebred cats. Ten cats were investigated, and in all ten cases there was a complete cure with cessation of tear flooding within 2–3 days of treatment. The effect of the treatment was at least as good as that obtained with steroid therapy. Finally, the same preparation was used as nasal drops for three cats with chronic recurrent upper air passage infections. One drop was applied to the nostrils morning and evening, and no other treatment was given. In all three cases the cats were completely free of symptoms of air passage infection after 2–3 days of treatment.

EXAMPLE 11

Rabbit eye tolerance test of sucralfate eye drops

The primary eye irritative effect of the sucralfate eye drops of Example 5 was tested in rabbits. The testing was done on four SPF albino female rabbits. Only the left eye was treated and the right eye served as an untreated control. About 0.1 ml of the test preparation was applied to the eye by gently pulling the lower eyelid away from the eyeball to form a cup into which the test substance was placed. The lids were then gently held together for about one second. The eyes were examined and the grade of occular reaction was recorded 1 hour later. 24 hours later an examination was performed before and after installation of ocoluguttae fluoresceini. After the examination the eyes were rinsed with 20 ml of a 0.9% sodium chloride solution. The eyes were also examined 48 and 72 hours after treatment. Cornea, iris and conjunctiva (including discharge) were inspected, and any reactions and changes were observed and scored. Slight discharge of conjunctiva was observed in two of the rabbits at the first examination. No reactions of conjunctiva, iris, or cornea were observed in any of the rabbits at the 24, 48 and 72 hour examinations.

Mean score values, as determined by a variety of different standard criteria, for cornea opacity, iris lesion, redness of conjunctiva and oedema of conjunctiva (chemosis) were all 0.0.

According to the criteria in the Official Journal of the European Communities, L 257, 1983, the directive of the commission, 83/467/EEC of Jul. 29, 1983, and the above mean values, it must be concluded that the tested sucralfate in a 2% aqueous suspension shall not be classified an eye irritant.

EXAMPLE 12

Prevention of thrombus formation with a central vein catheter with a sucralfate coating Thrombus formation due to a central vein silicone catheter was investigated with and without a sucralfate coating in a guinea pig model. The local tissue reaction to such catheters implanted in muscle tissue was also studied. Eight silicone catheters (7 French Silicone from Durascau Medical Products A/S, Odense) were used. Each catheter had a length of about 15 cm. Four catheters were coated by a dip-coating technique with a microcrystalline suspension of sucralfate (40% w/w), and the catheters were sterilized by radiation.

Silicone catheters (2 mm) were inserted surgically in the jugular vein, until the tip reached the level of the bijugular junction. The outer end of the catheter was bent and fixed to the muscle tissue close to the vein. The skin was closed according to routine procedures. Two other catheters were inserted transversely in the lumbar part of the longissimus dorsi muscle. Each catheter was inserted via a small medial skin wound and led out through another small skin wound, and then subcutaneously tunnelled back to the first skin wound. In guinea pig No. 1 the coated catheters were inserted on the right side and uncoated controls on the left side. In guinea pig No. 2 the position of catheters was the opposite.

Both guinea pigs were anaesthetized and exsanguinated one week after surgery. The quantity of thrombus masses around the intravasal catheters and on the vein was recorded. The intramuscular catheters were removed and pieces of muscle tissue and subcutaneous tissue around the catheter canal were isolated and fixed for subsequent microscopy.

No signs of overt reaction to the catheters were observed during the week from surgery to sacrifice. The weight of the thrombus formations found at the front end of the catheter was as follows:

| Guinea pig No. | Catheter | Thrombus weight (g) |
|---|---|---|
| 1 | Right (coated) | 0.49 |
| 1 | Left | 1.71 |
| 2 | Right | 0.28 |
| 2 | Left (coated) | 0.05 |

In the subcutaneous tissue no reaction was seen around any of the catheter canals. In the muscle tissue from both the right and left side, a very thin grayish zone was seen around the catheter canal. There was no difference in this respect between the right and left side. Microscopically, a subcutaneous membrane rich in mononuclear cells and small vacuoles was found along the catheter canal, and in the surrounding connective tissue foreign body giant cells were seen. There were no significant differences in this regard between coated and control sites.

EXAMPLE 13

The clinical effect of the potassium salt of sucrose octasulphate was investigated in a variety of infectious/inflammatory diseases in dogs and cats. The animals were recruited from a pet hospital, and the diseases treated thus reflect clinical relevant situations. A sterile solution of 20 mg/ml of the potassium salt was used in the following cases:

A dog with a fractured femoris undergoing osteosynthesis received the test preparation i.v. at 5 mg/kg body weight. Postoperatively, there was no temperature rise or other clinical symptoms on inflammation or infection.

A dog with chronic endometriosis undergoing panhysterectomy received the test preparation i.v. at 5 mg/kg body weight. Postoperatively, there was no temperature rise, a rapid decrease in neutrophiles and a quick convalescence.

A dog with a traumatic wound and tendon rupture received one ml of 20 mg/ml of the test preparation topically in the wound. Postoperatively, there was no suppuration and a rapid healing.

A cat undergoing hysterectomy received the test preparation i.v. at 5 mg/kg body weight, and postoperatively, there were no inflammatory wound reactions.

Two dogs with surgically treated arthritis had 5 ml of the test preparation applied topically in the joint and in the surrounding tissue in a concentration of 1 mg/ml in connection with surgery. Postoperatively, there was very little joint swelling and the dogs could stand upon their legs one day after operation.

Five cats suffering from chronic rhinitis in connection with cat's influenza received one injection of the test preparation in a concentration of 1 mg/ml i.v. in a dose of 1 mg/kg body weight, and the same preparation topically as one drop in each nostril B.D. In four of the cases, there was a significant clinical improvement, nasal discharge decreased and became less watery, and leucocytosis decreased.

One dog with aspiration pneumonia in connection with a revolved stomach received the test preparation i.v. in a concentration of 20 mg/ml and in a dose of 5 mg/kg body weight B.D. After 2 days, the temperature was normal, and auscultatoric pulmonal changes improved, and dyspnoea and coughing disappeared on day 4.

In no case, was there any sign of intolerance associated with the i.v. injection or of the topical application in surgical wounds of the potassium salt of the polysulphated saccharide sucrose octasulphate. The systemic i.v. treatment resulted in all of the cases in a clinical improvement which suggested a potent anti-inflammatory and anti-infective effect of the drug.

EXAMPLE 14

The effect of sucralfate against the production of interleukin-2 (IL-2) and interferon-gamma (INF-gamma)—both spontaneously produced and PHA-induced production—of normal mononuclear human cells was tested. An aqueous suspension of micronized (10 $\mu$m) sucralfate 100 mg/ml was diluted to 10, 1 and 0.1 mg/ml. The results showed that sucralfate by itself did not give rise to any activation of production of these two cytokines. There was a dose-related inhibition of the PHA-activated production of IL-2 (4, 40, 70 U/ml), and of INF-gamma (0, 100, >100 U/ml). It was concluded that sucralfate exerted an anti-inflammatory effect when tested in this in vitro model.

There was a sediment in the stock suspension of sucralfate 100 mg/ml, and mainly the supernatant was used when preparing the dilutions of 10, 1 and 0.1 mg/ml of sucralfate. The above-mentioned anti-inflammatory effect may therefore be due mainly to the sucralfate in solution which most likely is in the form of ionized sucrose octasulphate and aluminium ions, respectively. The anti-inflammatory effect demonstrated in this in vitro model is therefore an effect which most likely can be ascribed to the polysulphated saccharide sucrose octasulphate.

We claim:

1. A method for cosmetically treating skin to reduce wrinkles, the method comprising topically applying to affected skin areas a cosmetically effective amount of at least one compound selected from the group consisting of sulfated monosaccharides, sulfated disaccharides, and salts and complexes thereof.

2. The method according to claim 1 wherein the saccharide is a monosaccharide selected from the group consisting of xylose, fructose and glucose.

3. The method according to claim 1 wherein the saccharide is a disaccharide selected from the group consisting of sucrose, lactose, maltose and cellobiose.

4. The method according to claim 1 wherein the sulphated saccharide is combined with a non-sulphated polysaccharide.

5. The method according to claim 1 wherein the saccharide is a polysulphated mono- or disaccharide.

6. The method according to claim 5 wherein the polysulphated saccharide is sucrose octasulfate.

7. The method according to claim 1 wherein the substance with which the saccharide is complexed or with which it forms a salt is an alkali or alkaline earth metal, or Al, Zn, Cu, Zr, Ti, Bi, Mn or Os, or is an organic base.

8. The method according to claim 6 wherein the polysulphated saccharide is the potassium or sodium salt of sucrose octasulphate.

9. The method according to claim 6 wherein the composition comprising sucrose octasulfate further comprises one or more ingredients selected from the group consisting of sodium, potassium, aluminum, magnesium and calcium salts of an anion selected from the group consisting of chloride, carbonate, bicarbonate, citrate, gluconate, lactate, acetate, gluceptate and tartrate.

10. The method according to claim 6 wherein the polysulphated saccharide is the aluminum complex of sucrose octasulphate.

11. The method of claim 1 wherein the compound is applied twice daily.

12. The method of claim 1 wherein the compound is a sulfated monosaccharide, or a salt or complex thereof.

13. The method of claim 1 wherein the compound is a sulfated disaccharide, or a salt or complex thereof.

* * * * *